United States Patent [19]

Sublette

[11] Patent Number: 4,760,027

[45] Date of Patent: Jul. 26, 1988

[54] MICROBIOLOGICAL DESULFURIZATION OF GASES

[75] Inventor: Kerry L. Sublette, Tulsa, Okla.

[73] Assignee: Combustion Engineering, Inc., Windsor, Conn.

[21] Appl. No.: 849,646

[22] Filed: Apr. 9, 1986

[51] Int. Cl.$^4$ .............................................. A61L 9/01
[52] U.S. Cl. ................................... 435/266; 435/282; 435/262; 435/264
[58] Field of Search ............................. 435/282, 266

[56] References Cited

U.S. PATENT DOCUMENTS 2,975,103  3/1961  Kirshenbaum ...................... 435/282
4,206,288  6/1980  Detz et al. .......................... 435/282

OTHER PUBLICATIONS

Overath et al–Chem. Abst. vol. 102 (1985) 154,542q.

Koelle et al–Chem. Abst. vol. 100 (1984) p. 90863u.

Primary Examiner—Sam Rosen
Attorney, Agent, or Firm—Richard H. Berneike

[57] ABSTRACT

There is disclosed a method for desulfurizing gases by microbiological techniques which involve the use of chemoautotrophic bacteria of the Thiobacillus genus to convert sulfides to sulfates either as a sulfide removal process or as a process for producing biomass. More specifically, the invention involves the use of *Thiobacillus denitrificans* under aerobic conditions to oxidize sulfur compounds such as hydrogen sulfide to sulfate compounds. The process may be carried out by various techniques such as in a continuous bioreactor system using an immobilization matrix. The method is particularly suited to the disposal of hydrogen sulfide which has been otherwise removed from natural gas and producing a biomass byproduct.

12 Claims, 3 Drawing Sheets

MICROBIOLOGICAL DESULFURIZATION OF GASES

BACKGROUND OF THE INVENTION

This invention relates to the desulfurization of gases and, in particular, relates to the microbiological disposal of hydrogen sulfide which has been otherwise removed from natural gas.

Natural gas from a well may contain a number of undesirable components which must be reduced to acceptable levels prior to distribution and sale. One of the most common problems in the gas industry is the removal and disposal of hydrogen sulfide. Hydrogen sulfide is an acid gas which is toxic and quite corrosive in the presence of water. Natural gas destined for the fuel market ordinarily must contain no more than 0.25 grains per 100 standard cubic feet or 4 ppm on a volume basis.

The most commercially important treatment system for the removal and disposal of hydrogen sulfide from natural gas consists of a combination of the amine process for removal from the gas stream followed by the Claus process for sulfur recovery. In the amine process, after contacting the gas stream, the amine solvent is heated to 200°–300° F. to liberate $H_2S$ and regenerate the solvent which is recycled. It is important to note that the $H_2S$ is removed from the gas stream but that it still must be disposed of. Hydrogen sulfide liberated during regeneration of the amine solvent is converted to elemental sulfur by the Claus process. In the Claus process, one third of the $H_2S$ of the acid gas stream received from the amine unit is burned with a stoichiometric amount of air to produce sulfur dioxide according to Equation (1). If the entire acid gas stream is fed to the reaction furnace, some conversion of $H_2S$ to elemental sulfur occurs in the furnace according to Equation (2). Further conversion is achieved by passing the reaction gas through a series of catalytic reactors where elemental sulfur formation proceeds more toward completion at lower temperatures. Alternately, one third of the acid gas stream may be fed to the reaction furnace for complete combustion of $H_2S$ to $SO_2$. The $SO_2$ is then mixed with the remaining acid gases and fed to the catalytic reactors.

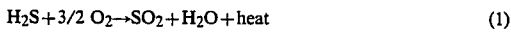
$$H_2S + 3/2\, O_2 \rightarrow SO_2 + H_2O + \text{heat} \tag{1}$$

$$2H_2S + SO_2 \rightleftharpoons 3S + 2H_2O + \text{heat} \tag{2}$$

The Claus process produces a high quality elemental sulfur product and salvage heat value as process credits which have a significant positive impact on the economics of the process. However, there are inherent limitations and operating problems which may adversely affect the economics of the application of the process to $H_2S$ disposal. These include the following:

(1) The maximum conversion efficiency with as many as three catalytic reactors in series is only 96–97%. Further treatment of the Claus tail gas may be required to meet local air quality standards.

(2) Conversion efficiency is sensitive to variations in the concentration of $H_2S$ in the acid gas feed stream.

(3) In the presence of carbon dioxide ($CO_2$) and light hydrocarbons, side reactions can result in the formation of carbonyl sulfide (COS) and carbon disulfide ($CS_2$) in the reaction furnace. The presence of COS and $CS_2$ may increase the number of catalytic stages requires for adequate $H_2S$ conversion since COS and $CS_2$ hydrolysis requires higher temperatures than those which favor conversion of $H_2S$ to elemental sulfur according to Equation (2).

(4) At $H_2S$ concentrations of less than 40% the temperature of the reaction furnace is insufficient to result in complete combustion of entrained hydrocarbons in the acid gas stream. Hydrocarbon reaction products can result in deactivation of the catalyst.

(5) Combustion of $H_2S$ in the reaction furnace becomes more unstable with decreasing concentration of $H_2S$ in the acid gas feed stream. At very low $H_2S$ concentrations (less than 20%) preheating of air and acid gas streams is required. In addition $SO_2$ must be generated by burning recycled elemental sulfur to ensure a proper stoichiometric $H_2S/SO_2$ ratio in the feed to the catalytic reactors.

With sufficient $H_2S$ available, a Claus plant can be profitable and offset other costs associated with natural gas treatment with sulfur sales and recovery of heat values. The break even point is influenced by those factors discussed above. However, because of increasingly stringent air quality standards for sulfur emissions, the Claus process has been applied in many treating situations where it is not economical. A need clearly exists for a new more economical technology in these situations especially with regard to acid gas streams with low concentrations of $H_2S$. A new technology which featured a saleable byproduct and greater conversion efficiency could also conceivably displace the Claus process in treating situations where it is presently regarded as economical. (Reference: Kohl, Arthur L. and Fred C. Riesenfeld, *Gas Purification*, Gulf Publishing Co., Houston, Tex., 3rd Ed., p. 410–421 (1979)).

MICROBIAL REMOVAL OF HYDROGEN SULFIDE FROM A GAS

A number of microbial processes for the oxidation of $H_2S$ have been described in the foreign patent literature. Those describing water treatment are generally based on the innoculation of wastewaters with *Thiobacillus thioparus* or other unspecified sulfur bacteria followed by aeration. (Polish Patent No. 98,513, Czechoslovakian Patent No. 178,012, U.S.S.R. Patent No. 1,070,120 and Polish Patent No. 106,991). *T. thioparus* has also been used to remove $H_2S$ from a gas which is bubbled through the culture (U.S.S.R. Patent No. 986,469). Mixed cultures of bacteria from the Beggiatoa and Thiothrix genera have been utilized in a similar manner (Japanese Patent No. 57,170,181). *Thiobacillus ferroxidans* has been used as the basis of two gas treatment processes in which $H_2S$ is first precipitated as CuS or FeS. The sulfide precipitant is subsequently oxidized by the organism regenerating the precipitating agent (West German Patent No. 3,300,402 and Japanese Patent No. 58,152,488). All of these processes are aerobic. The latter two require a very low, corrosion inducing pH.

A microbial process for the removal of $H_2S$ from a gas stream based on the photosynthetic bacterium *Chlorobium thiosulfatophilum* has been proposed as an alternative to the Claus or Stretford process. (Cork, D. J., "Acid Gas Bioconversion—An Alternative to the Claus Process," Dev. Ind. Micro., 23, 379–387 (1982); Cork, D. J. and S. Ma., "Acid Gas Bioconversion Favors Sulfur Production," Biotech. and Bioeng. Symp. No. 12, 285–290 (1982); and Cork, D. J., R. Garunas and A. Sajjad, "*Chlorobium limicola* forma *thiosulfatophilum*: Biocatalyst in the Production of Sulfur and Organic Carbon from a Gas Stream Containing $H_2S$ and $CO_2$,"

Appl. and Env. Micro., 45, 913-918 (1983)). The process converts H₂S into a mixture of elemental sulfur and sulfate and claims sulfur and biomass as process credits. However, the requirement for radiant energy is a severe economic disadvantage whether supplied artificially or collected from sunlight.

SUMMARY OF THE INVENTION

An object of the present invention is to provide a method for desulfurizing gases by microbiological techniques. More particularly, the invention involves the use of chemoautotrophic bacteria of the Thiobacillus genus to convert sulfides to sulfates either as a sulfide removal process or as a process for producing biomass. More specifically, the invention involves the use of *Thiobacillus denitrificans* under essentially aerobic conditions to oxidize sulfur compounds such as hydrogen sulfide to sulfate compounds. A particular embodiment of the invention includes the use of specific strains of *Thiobacillus denitrificans* which will withstand high sulfide concentrations and be resistant to a common biocide. The process of the invention may be carried out by various techniques such as in a continuous bioreactor system. The invention is particularly applicable to the disposal of H₂S which has been otherwise removed from natural gas and producing a biomass byproduct.

DESCRIPTION OF PREFERRED EMBODIMENTS

Introduction

Figure 1:
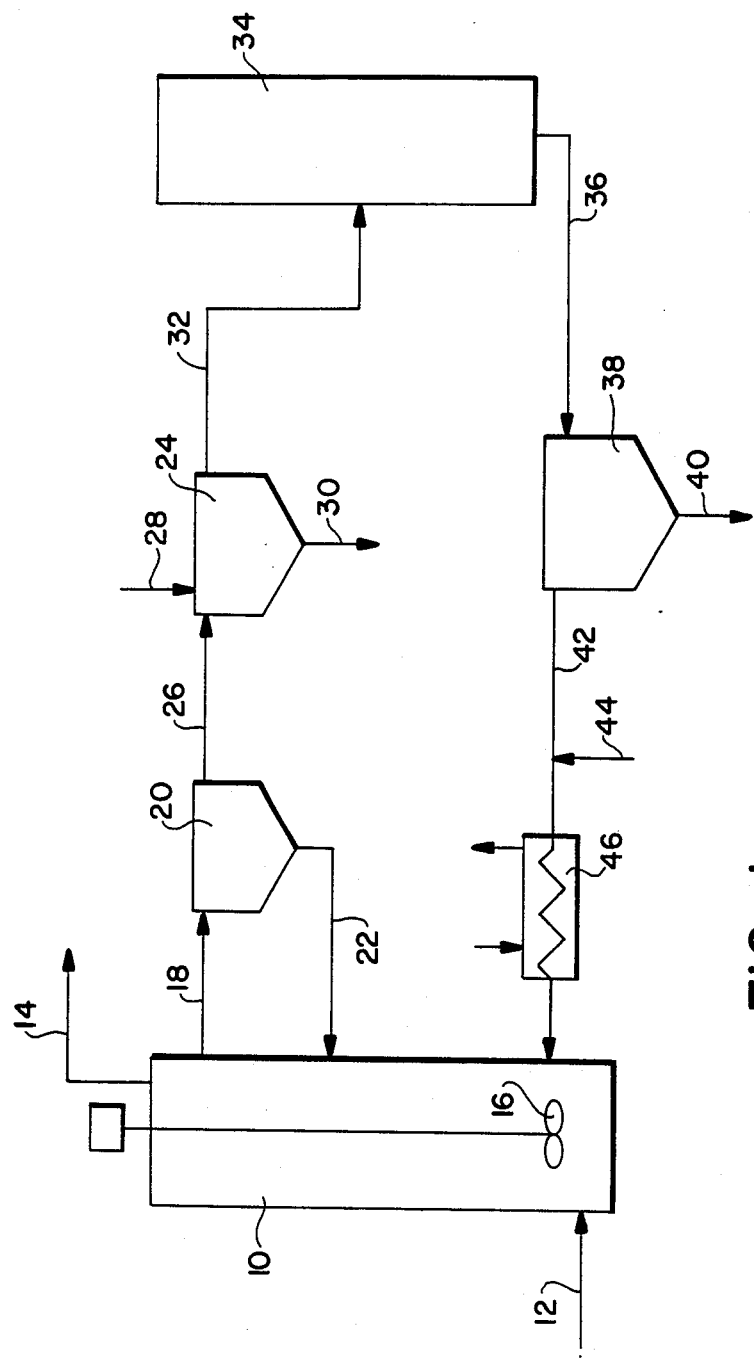
FIG. 1 is a flow diagram of the preferred embodiment of the invention.

With the exception of photosynthetic organisms, the majority of the biological world derives energy from the oxidation of organic compounds. However, there exists a group of microorganisms, predominantly bacteria, which may derive metabolic energy and reducing equivalents for biosynthesis from the oxidation of inorganic elements and compounds. These microorganisms may also derive carbon for biosynthesis from an inorganic source such as carbon dioxide. This is termed a chemoautotrophic mode of metabolism. The present invention employs such bacteria and such mode of metabolism in order to remove sulfides from gas streams.

A microbial gas desulfurization process offers several advantages which could make the process commercially viable. These include the following:

1. Direct conversion of hydrogen sulfide to sulfate is possible with no requirement for secondary sulfur recovery.

2. The energy requirements are low since the process operates at ambient or near ambient temperatures.

3. The nutrient is predominantly inexpensive mineral salts resulting in a low cost for chemicals.

4. The pH is moderate so that there are minimal corrosion problems.

5. No hazardous wastes are generated and there are minimal disposal problems.

6. The process produces a high protein biomass and a sulfate salt which could represent salable products.

The ideal microorganism upon which to base a microbial hydrogen sulfide removal process must possess several characteristics in addition to the ability to oxidize hydrogen sulfide. The ideal microorganism would have simple nutritional requirements in order to minimize chemical costs. Preferably the organism would be a strict autotroph, that is, the organism would be capable of deriving all of its metabolic needs from inorganic sources. The ideal organism would also be capable of hydrogen sulfide oxidation in an anaerobic as well as an aerobic environment to give greater versatility to the process. Preferably, the ideal organism would produce a soluble oxidation product from the hydrogen sulfide in order to facilitate separation of the oxidation product from the biomass. The ideal organism would also exhibit a small size and simple morphology so that it can be easily maintained in suspension. Many microorganisms produce an extracellular slime layer or capsid which can cause the microorganisms to adhere to walls and to each other. The ideal organism for hydrogen sulfide removal applications would not produce a capsid in order to prevent problems in transport of the organism. A useful organism would also be able to withstand high pressures and moderately high temperatures. An optimal pH near neutral would be desirable in order to minimize corrosion. And, of course, the ideal microorganism would also exhibit a high rate of hydrogen sulfide oxidation per unit biomass.

Many chemolithotrophic bacteria are capable of utilizing the oxidation of elemental sulfur and reduced or partially reduced sulfur compounds as a source of energy and reducing equivalents. However, taking into consideration the above factors, the bacterium *Thiobacillus denitrificans* has been discovered to be uniquely suitable for the objects of the present invention.

Thiobacillus denitrificans

*Thiobacillus denitrificans* (*T. denitrificans*) was first isolated in 1904 by innoculation of an aqueous medium containing $MgCl_2$, $K_2HPO_4$, $KNO_3$, $Na_2CO_3$ and a sediment of elementary sulfur and $CaCO_3$ with canal water or mud. A bacterial flora developed which oxidized the sulfur to sulfate and simultaneously reduced nitrate to elemental nitrogen. This was the first evidence of the existence of a chemolithotropic bacterium which could survive in the absence of oxygen. It was subsequently shown that thiosulfate could be substituted for elemental sulfur. It was later demonstrated that a reduced nitrogen source was required for growth and *T. denitrificans* was cultivated in a defined medium for the first time. (Baalsrud, K. and K. S. Baalsrud, "Studies on *Thiobacillus denitrificans*," Arch. Mikro., 20, 34–62 (1954)). This achievement led to the first thorough study of the growth characteristics of the bacterium. These same authors reported the following:

(1) *T. denitrificans* is a facultative anaerobe utilizing oxygen under aerobic conditions or nitrate under anaerobic conditions as terminal electron acceptor.

(2) *T. denitrificans* is an obligatory autotroph; that is, it cannot derive its metabolic needs from organic sources but is strictly dependent upon elemental sulfur and reduced sulfur compounds as energy sources and carbon dioxide as a carbon source.

(3) Nitrate cannot serve as a sole source of nitrogen. Ammonia nitrogen is required for growth.

(4) Iron is required for growth. Good growth was reported in media containing 0.25–8.3 micrograms Fe/ml.

(5) The optimum pH for growth of *T. denitrificans* is in the range of 6.2–7.0. The organism is rapidly deactivated below pH 6.0.

Although it has been amply demonstrated that thiosulfate and elemental sulfur may be utilized as energy sources with oxidation to sulfate, the utilization of sulfide as an energy source by *T. denitrificans*, as well as other Thiobacilli, has been the subject of some controversy in the past. Some investigators have reported that cultures of *T. denitrificans* provided with sulfide, usually supplied as $Na_2S$, as the sole energy source failed to show an increase in protein content or sulfate concentration in batch reactors. Others have observed the oxidation of sulfide by whole cells or cell free extracts of *T. denitrificans* and other Thiobacilli. The deposition of elemental sulfur in growing cultures has been observed causing some investigators to speculate that sulfide was oxidized to elemental sulfur and thiosulfate purely chemically and that these products were the true substrates for the Thiobacilli. It is now apparent that those investigators who reported that *T. denitrificans* was incapable of growth on sulfide as an energy source came to an erroneous conclusion due to the very high initial sulfide concentrations used in their experiments (5–8 mM). Soluble sulfide is toxic to Thiobacilli, as well as other microorganisms, in elevated concentrations. It has been demonstrated that *T. denitrificans* will grow anaerobically on sulfide ($Na_2S$) as an energy source if sulfide is used as the growth limiting factor in a chemostat. (Timmer-ten Hoor, A., "Energetic Aspects of the Metabolism of Reduced Sulphur Compounds in *Thiobacillus denitrificans*," Antonie van Leeuwenhoek, 42, 483–492 (1976)). Under these conditions, the concentration of sulfide in the culture is maintained at very low levels and sulfide is oxidized to sulfate. Although this work established the ability of *T. denitrificans* to utilize sulfide as an energy source under anaerobic and sulfide limiting conditions, growth on $H_2S$ under aerobic conditions had not been demonstrated prior to this work.

Growth and Maintenance of Cultures

The routine maintenance of *T. denitrificans* for stock cultures in a medium containing sulfide as an energy source would require continuous or semi-continuous addition of sulfide in such a way that sulfide did not accumulate to inhibitory levels in the culture but sufficient substrate was made available for growth. Although this could be done within the scope of the present invention, the obvious difficulties associated with routine day-to-day maintenance of cultures in a sulfide medium can be avoided by use of a non-toxic substrate, preferably thiosulfate. A typical thiosulfate maintenance medium is given by Tables 1 to 3.

TABLE 1

| Maintenance Medium | |
|---|---|
| Component | per liter |
| $Na_2HPO_4$ | 1.2 g |
| $KH_2PO_4$ | 1.8 g |
| $MgSO_4.7H_2O$ | 0.4 g |
| $NH_4Cl$ | 0.5 g |
| $CaCl_2$ | 0.03 g |
| $MnSO_4$ | 0.02 g |
| $FeCl_3$ | 0.02 g |
| $NaHCO_3$ | 1.0 g |
| $KNO_3$ | 5.0 g |

TABLE 1-continued

| Maintenance Medium | |
|---|---|
| Component | per liter |
| $Na_2S_2O_3$ | 10.0 g |
| Heavy metal solution | 15.0 ml |
| Mineral water | 50.0 ml |

TABLE 2

| Heavy Metal Solution | |
|---|---|
| Component | per liter |
| EDTA (Ethylenediaminetetraacetic acid) | 1.5 g |
| $ZnSO_4.7H_2O$ | 0.1 g |
| Trace element solution | 6.0 ml |

TABLE 3

| Trace Element Solution | |
|---|---|
| Component | per liter |
| $AlCl_3.6H_2O$ | 0.51 g |
| KI | 0.14 g |
| KBr | 0.14 g |
| LiCl | 0.14 g |
| $H_3BO_3$ | 3.06 g |
| $ZnCl_2$ | 0.28 g |
| $CuCl_2.2H_2O$ | 0.33 g |
| $NiCl_2.6H_2O$ | 0.51 g |
| $CoCl_2.6H_2O$ | 0.51 g |
| $SnCl_2.2H_2O$ | 0.14 g |
| $BaCl_2.2H_2O$ | 0.16 g |
| $Na_2MoO_4.2H_2O$ | 0.16 g |
| $CuSeO_4.5H_2O$ | 0.14 g |
| $NaVO_3$ | 0.024 g |

The thiosulfate in the maintenance medium is the energy source, nitrate is the terminal electron acceptor allowing growth in the absence of oxygen, bicarbonate is the carbon source and ammonium is the nitrogen source. The medium also includes a phosphate buffer and sources of various essential mineral nutrients. This maintenance medium is similar to the S-8 medium for Thiobacilli recommended by the American Type Culture Collection except that ammonium chloride has been substituted for ammonium sulfate as the source of reduced nitrogen with an increase in the concentration of ammonium ion, the concentrations of sodium bicarbonate and hydrated magnesium sulfate have been increased and a known source of trace elements has been added.

Oxidation of Hydrogen Sulfide

To produce a culture of *T. denitrificans* to be utilized for the removal of $H_2S$ from a gas, the organism is typically grown aerobically in the thiosulfate maintenance medium without nitrate at 30° C. and a pH of 7.0 to an optical density at a wavelength of 460 nanometers ($OD_{460}$) of approximately 1.0. This optical density corresponds to greater than $10^9$ cells per ml. As has previously been indicated, the purpose of this cultivation on thiosulfate is to develop a sufficient concentration of biomass so that hydrogen sulfide can be fed to the reactor at an appreciable rate without exceeding the bio-oxidation capabilities of the biomass. Otherwise, sulfide accumulates in the culture. During growth on thiosulfate an aeration rate of 200 to 300 ml/min/l of culture is used. It is advisable to supplement the air feed with 5% $CO_2$ to ensure continuous availability of a carbon source.

The pathways for sulfide and thiosulfate oxidation to sulfate in *T. denitrificans* are not independent but have two common intermediates. In the presence of thiosulfate the rate of sulfide oxidation is reduced because of competition for enzymes of the sulfur pathway. Therefore, there should be no residual thiosulfate in the culture when $H_2S$ is introduced. This is readily accomplished by cultivating the cells to the point that all thiosulfate has been metabolized. The yield of *T. denitrificans* biomass on thiosulfate as an energy source has been observed to average 6.7 g dry wt./mole in batch reactors. The desired concentration of biomass can be developed by adjusting the thiosulfate concentration in the medium with the precaution that the medium be thiosulfate limiting. When thiosulfate is depleted, $H_2S$ may be introduced into the reactor at loadings of 8–10 mmoles/hr/g dry wt. of biomass. The culture must be sufficiently aerated that the reaction does not become oxygen limiting. Oxygen limitation has been observed at bulk oxygen concentrations below approximately 25 $\mu M$.

When $H_2S$ is introduced to a culture of *T. denitrificans* previously grown on thiosulfate, the $H_2S$ is immediately metabolized with no apparent lag. Under sulfide limiting conditions, less than 0.001 mM of total sulfide can be detected in the reactor medium. Provided then that the feed gas exits the reactor in equilibrium with the medium, very low levels of $H_2S$ in the outlet gas can be achieved (less than 1 ppmv). With 10,000 ppm $H_2S$ in the feed gas at one atmosphere, residence times in the range of 1–2 sec are required if the average bubble diameter is approximately 0.25 cm.

The introduction of $H_2S$ into a batch *T. denitrificans* reactor results in the accumulation of sulfate and biomass with a corresponding decrease in the ammonium concentration. No elemental sulfur accumulates in the reactor. The stoichiometry of the reaction in a batch reactor is given by Table 4.

TABLE 4

| Stoichiometry of Aerobic $H_2S$ Oxidation by *T. denitrificans* in Batch Reactors[a] ||
|---|---|
| $SO_4^{-2}/H_2S$ | 0.99 ± 0.05 mole/mole |
| $O_2/H_2S$ | 1.81 ± 0.11 mole/mole |
| $NH_4^+/H_2S$ | 0.10 ± 0.02 mole/mole |
| $OH^-/H_2S$ | 1.75 ± 0.16 equivalents/mole |
| Biomass/$H_2S$ | 4.5 ± 0.9 grams/mole |

[a]95% confidence intervals

Certain aspects of the stoichiometry of any microbial process are affected by the environment and the growth rate of the microbial cells. During batch growth these parameters are constantly changing. In a continuous stirred tank reactor (CSTR) where a fresh nutrient feed (maintenance medium minus nitrate and thiosulfate) is fed to the reactor at the same rate at which mixed liquor is removed from the reactor, and where there is complete mixing, the environment and growth rate are held constant. Each of these parameters is controlled by the dilution rate at which the reactor is operated. The dilution rate D is defined by Equation (3) where q is the volumetric flow rate of nutrient to the reactor and v is the culture volume.

$$D = q/v \qquad (3)$$

The stoichiometry of aerobic oxidation of $H_2S$ by *T. denitrificans* in a CSTR at dilution rates of 0.053 $hr^{-1}$ and 0.030 $hr^{-1}$ is given in Table 5. The yield of biomass was expected to be greater at the higher dilution rate since a greater fraction of substrate $H_2S$ would be expected to support biosynthesis at higher growth rates. This has been observed to be the case under anaerobic conditions. However, biomass yield from aerobic growth on $H_2S$ was nearly the same at the two dilution rates investigated.

TABLE 5

| Stoichiometry Of Aerobic $H_2S$ Oxidation By *T. denitrificans* in Continuous Flow Reactors[a] |||||
|---|---|---|---|---|
| Dilution Rate ($hr^{-1}$) | $SO_4^{-2}/H_2S$ (mole/mole) | $NH_4^+/H_2S$ (mole/mole) | $OH^-/H_2S$ (eq./mole) | Biomass/$H_2S$ (g/mole) |
| 0.053 | 1.04 ± 0.06 | 0.12 ± 0.01 | 1.77 ± 0.23 | 7.9 ± 0.7 |
| 0.030 | 1.06 ± 0.09 | 0.11[b] | 2.38[b] | 8.1 ± 2.0 |

[a]95% confidence intervals
[b]average of two determinations

It has been reported in the literature that oxygen acts as an inhibiting substrate for *T. denitrificans* while growing aerobically on thiosulfate. Highest yields of biomass have been observed at low steady state oxygen concentrations in the culture medium. (Reference: Justin, P. and D.P. Kelly, "Metabolic Changes in *Thiobacillus denitrificans* Accompanying the Transition from Aerobic to Anaerobic Growth in Continuous Chemostate Growth", J. Gen. Micro., 107, 131–137 (1978). As shown in Table 6, experiments have not shown oxygen concentration in the range of 45–150 $\mu M$ to have a discernable effect on biomass yield for aerobic growth of *T. denitrificans* on $H_2S$.

TABLE 6

| Biomass Yield As A Function of Steady State Oxygen Concentration and Dilution Rate |||
|---|---|---|
| Dilution Rate ($hr^{-1}$) | $[O_2]$ ($\mu M$) | Yield (g Biomass/mole $H_2S$) |
| 0.053 | 45 | 8.4 |
|  | 60 | 7.7 |
|  | 150 | 7.3 |
|  | 130 | 7.6 |
|  | 150 | 8.5 |
| 0.030 | 90 | 7.7 |
|  | 120 | 9.0 |
|  | 100 | 7.5 |

Indications of Upset and Recovery from Upset Conditions

Since $H_2S$ is an inhibitory substrate, it is imperative that the $H_2S$ feed rate to a *T. denitrificans* reactor not exceed the maximum capacity of the biomass for $H_2S$ oxidation. If the $H_2S$ oxidation capacity of the biomass is exceeded, sulfide will accumulate in the reactor medium and inhibit the complete oxidation of $H_2S$. Reactor upset is first indicated by an increase in the optical density of the culture due to elemental sulfur accumulation. The culture takes on a whitish appearance. This is followed by $H_2S$ breakthrough. The upset condition is reversible if exposure to the accumulated sulfide is not more than 2 to 3 hours. Reduction in $H_2S$ feed rate following an upset condition will reduce the $H_2S$ concentration in the outlet gas to pre-upset levels. In addition, elemental sulfur which accumulated during upset will be oxidized to sulfate upon reduction in $H_2S$ feed rate. The duration of the upset condition dictates the amount of reduction in the feed rate required for recovery. The more sustained the period of upset, the more reduction in feed rate required. The maximum loading of a *T. denitrificans* culture will be somewhat dependent upon both the metabolic state (growth rate) of the biomass and the environment of the biomass. Maximum loadings in the range of 16 to 20 mmoles $H_2S$/hr/g dry wt. biomass may be expected under aerobic conditions.

Effect of Heterotrophic Contamination

The medium described by Tables 1–3 will not support the growth of heterotrophic microorganisms since there is no organic carbon source. However, if aseptic conditions are not maintained in the operation of a *T. denitrificans* reactor, heterotrophic contamination will develop in the reactor. *T. denitrificans* releases organic material into the medium in the normal course of growth or through lysis of nonviable cells. This organic material then supports the growth of heterotrophs. In a *T. denitrificans* CSTR operated nonaseptically, the concentration of heterotrophic contaminants will level off and remain constant after a time. The steady state concentration of contaminant is not surprisingly dependent upon the concentration of *T. denitrificans*. Contaminant levels of up to 10% of the *T. denitrificans* concentration can be expected. Although the presence of a heterotrophic contamination can affect the end use of the biomass product of the process, the contamination does not affect $H_2S$ oxidation by *T. denitrificans*.

Characterization of *Thiobacillus denitrificans*

Other factors pertinent to the operation of a microbial gas desulfurization process include the effects temperature and pressure, the toxicity of other sulfur compounds which may contaminate the feed gas, the effects of accumulating sulfate on cell activity and the effect on viability of maintenance in liquid culture in the absence of an energy source.

Each of these parameters was examined under conditions in which *T. denitrificans* could be most easily cultured on a small scale, namely anaerobically in thiosulfate maintenance medium. Conclusions reached under these conditions are likely to be pertinent to aerobic growth on $H_2S$. As indicated previously, *T. denitrificans* cells grown on thiosulfate will readily oxidize $H_2S$ with no lag. It has also been observed that *T. denitrifications* cells growing on $H_2S$ can be switched back and forth between aerobic to anaerobic conditions with no apparent lag in either direction. These results indicate that under any of these growth conditions the cells contain basically the same complement of enzymes.

Figure 2:
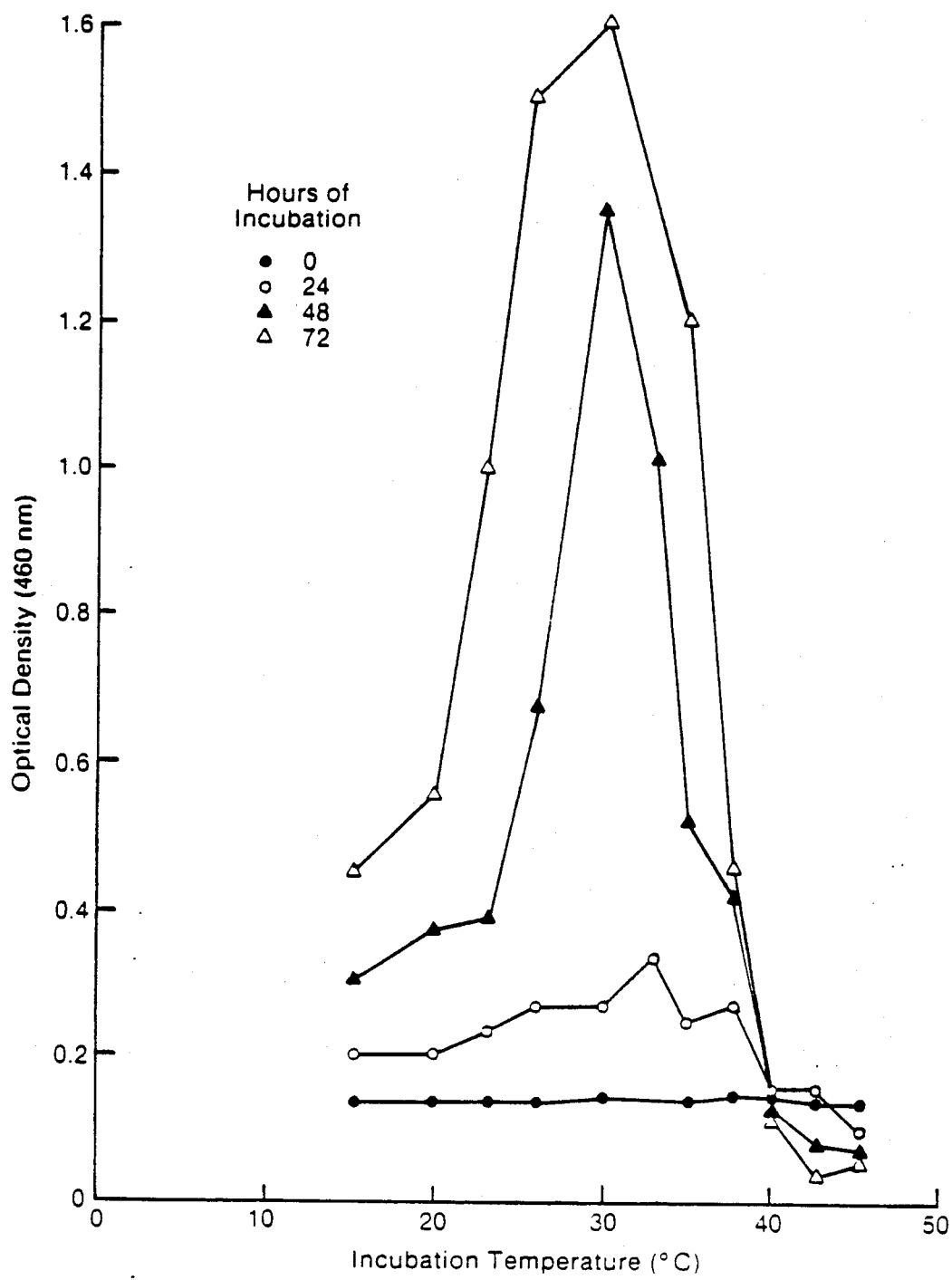
FIG. 2 is a graph showing the effect of temperature on the growth of *Thiobacillus denitrificans*.

The optimum temperature for growth of *T. denitrificans* has been reported as 30° C. However, a temperature profile indicating relative growth rates above and below this optimum has not been published. A temperature profile is necessary to predict the effects of a temperature excursion or temperature gradients on overall and local growth rates in a culture. This can be especially important in the case of an inhibitory substrate where a general or localized decrease in growth rate could result in accumulation of the substrate to toxic concentrations. A temperature profile for *T. denitrificans* ATCC 23642 growing anaerobically on thiosulfate is given in FIG. 2 which indicates optimal growth over a relatively narrow range of temperatures with complete inhibition of growth above 40° C. However, viable counts have shown that at temperatures as high as 45° C., no measurable effect on viability is observed for exposures of up to 5 hours.

Growth of *T. denitrificans* in thiosulfate medium at 30° C. at elevated pressures indicates that total pressure has no significant effect on growth at pressures of up to 1800 psig $N_2$ or 1000 psig $CH_4$. These results are shown in Table 7. Viability was demonstrated at the conclusion of each test by growth on thiosulfate agar and no heterotropic contamination was indicated in that no growth appeared on nutrient agar. In a microbial gas desulfurization process the microorganisms may be subjected to rapid pressurization-depressurization cycles. Table 8 summarizes the results of rapid pressurization-depressurization at 1250 psig of $N_2$ on viable count in a culture of *T. dentrificans* originally grown at that pressure on thiosulfate. Table 8 indicates that repeated pressurization-depressurization has no significant effect on viability.

TABLE 7

Effect of Pressure on Growth of *T. denitrificans* on Thiosulfate in Liquid Culture

| Culture | Press. (psig) | Gas | Incubation Time (days) | Optical Density (460 nm) |
|---|---|---|---|---|
| TEST | 400 | $N_2$ | 3 | 1.10 |
| CONTROL | 0 | | 3 | 1.14 |
| TEST | 600 | $N_2$ | 4 | 1.05 |
| CONTROL | 0 | | 4 | 1.20 |
| TEST | 750 | $N_2$ | 3 | 0.75 |
| CONTROL | 0 | | 3 | 1.20 |
| TEST | 1000 | $N_2$ | 3 | 0.75 |
| CONTROL | 0 | | 3 | 1.00 |
| TEST | 1240 | $N_2$ | 3 | 0.75 |
| CONTROL | 0 | | 3 | 0.83 |
| TEST | 1800 | $N_2$ | 3 | 1.08 |
| CONTROL | 0 | | 3 | 0.87 |
| TEST | 500 | $CH_4$ | 3 | 0.85 |
| CONTROL | 0 | | 3 | 0.80 |
| TEST | 1000 | $CH_4$ | 3 | 1.20 |
| CONTROL | 0 | | 3 | 0.62 |

TABLE 8

Effect of Sequential Pressurization-Depressurization Cycles at 1250 psig $N_2$ on Viability of *T. denitrificans* in Liquid Culture

| Pressurization/ Depressurization Cycles | Viable Count (cells/ml) |
|---|---|
| 0 | $5.2 \times 10^8$ |
| 1 | $3.9 \times 10^8$ |
| 2 | $4.2 \times 10^8$ |
| 3 | $3.4 \times 10^8$ |
| 4 | $4.3 \times 10^8$ |

Various sulfur compounds common to natural gas are somewhat toxic to *T. denitrificans*. Those compounds are methyl mercaptan ($CH_3SH$), carbon disulfide ($CS_2$), carbonyl sulfide (COS) and dimethyl sulfide ($CH_3SCH_3$). The order of toxicity to wild type *T. denitrificans* is $CH_3SH > CS_2 > COS$, $CH_3SCH_3$. All are toxic at a partial pressure of 200 mmHg. At partial pressures sufficiently low to be tolerated none are metabolized.

As $H_2S$ is oxidized by *T. denitrificans*, a sulfate salt accumulates in the medium. Under aerobic conditions, the counter ion of the sulfate in this salt will be determined by the counter ion of the hydroxide equivalents added to the culture to maintain pH. For example, if KOH is the alkali used for pH control, the oxidation product of $H_2S$ is primarily present as $K_2SO_4$. Whether the reactor is operated batchwise or on a continuous basis, the concentration of sulfate salt will be dependent upon the rate of $H_2S$ oxidation per unit volume of culture. The tolerance of *T. denitrificans* for the accumulating sulfate salt, therefore, has a major influence on the operation of the reactor. Wild type *T. denitrificans* is tolerant of up to 450 nM $K_2SO_4$ when grown anaerobically on $H_2S$. Above approximately 500 mM, incomplete oxidation of $H_2S$ is observed with the accumulation of elemental sulfur and production of $N_2O$ from incomplete reduction of nitrate. The organism is less tolerant of $Na_2SO_4$; however, normal reactor operation is observed at $Na_2SO_4$ concentrations of 300–400 mM. $(NH_4)_2SO_4$ causes incomplete $H_2S$ oxidation at concentrations above 150–200 mM.

Figure 3:
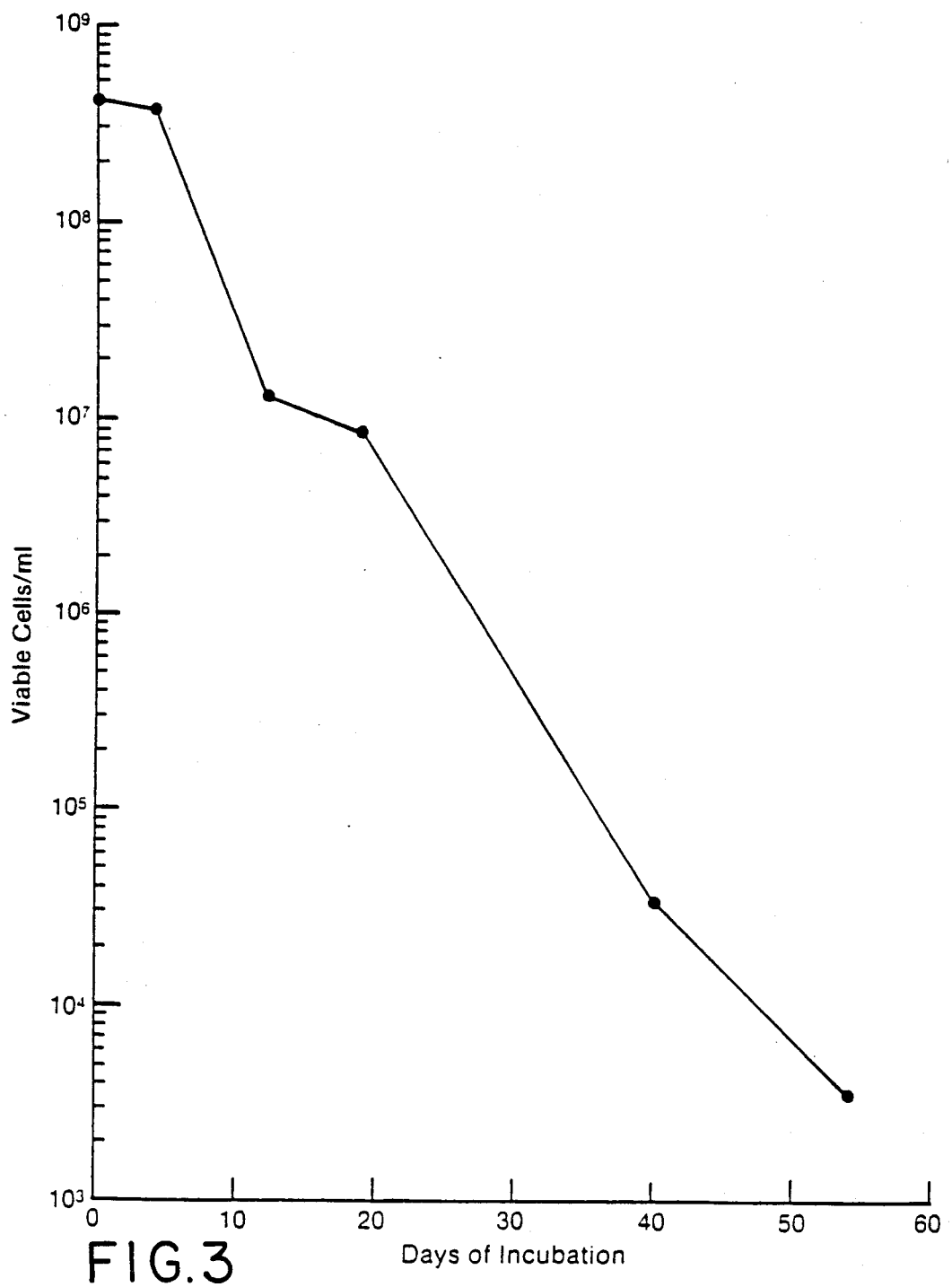
FIG. 3 is a graph showing the viability of *Thiobacillus denitrificans* in free suspension in liquid medium without an energy source.

As noted above, another factor pertinent to the operation of a microbial gas desulfurization process is the effect on viability of maintenance in liquid culture in the absence of an energy source as would occur if the feed gas to the process were shut off for a period of time. As illustrated by FIG. 3, the viable count in a culture of *T. denitrificans* decreases with time in the absence of an energy source. However, if a working culture contains at least $10^9$ cells/ml, a sufficient number of viable cells will exist after as much as 20 days to provide an adequate innoculum to restart the process if care is taken not to overload the biomass.

Another factor which will influence the economics of a microbial gas desulfurization process is the value of the biomass produced. The protein content of *T. denitrificans* whole cells grown on $H_2S$ is 60%±3% by dry weight. This protein content is intermediate between that of soybeanmeal (51%) and fish meal. (72%), the two most commercially important sources of bulk protein. The quality of a bulk protein source as a food supplement is dependent not only upon the protein content but also upon the amino acid composition of that protein. Table 9 gives the amino acid composition of *T. denitrificans* whole cell protein when the organism is grown on $H_2S$. Table 10 compares the amino acid composition of *T. denitrificans* whole cell protein, with respect to the ten essential amino acids in a mammalian diet, to that of soybeam meal and fish meal Table 10 indicates that *T. denitrificans* whole cell protein, on a g/100 g basis, contains more of nine of these amino acids than soybeam meal. The only possible exception is tryptophan which has not been determined for *T. denitrificans* protein. Fish meal contains greater quantities of isoleucine, lysine, threonine and possibly tryptophan. The cysteine content of *T. denitrificans* is so low as to be undetectable. Also pertinent to the nutritional quality of the biomass is the mineral content. A trace element analysis of *T. denitrificans* biomass grown on $H_2S$ is given in Table 11.

TABLE 9

Amino Acid Composition of *T. denitrificans* Whole Cell Protein

| Amino Acid | g/100 g Protein |
|---|---|
| Alanine | 7.8 |
| Arginine | 7.3 |
| Aspartic Acid + Asparagine | 10.3 |
| Glutamic Acid + Glutamine | 11.1 |
| Glycine | 5.2 |
| Histidine | 5.5 |
| Isoleucine | 5.4 |
| Leucine | 9.7 |
| Lysine | 7.1 |
| Methionine | 3.7 |
| Phenylalanine | 4.4 |
| Proline | 4.4 |
| Serine | 3.4 |
| Threonine | 4.4 |
| Tyrosine | 3.7 |
| Valine | 6.7 |

TABLE 10

Essential Amino Acid Content of *T denitrificans* Protein Compared to Soybean Meal and Fish Mean Proteins

| | g/100 g Protein | | |
|---|---|---|---|
| Amino Acid | Soybean Meal | Fish Meal | *T. denitrificans* |
| Arginine | 6.2 | 6.8 | 7.3 |
| Histidine | 2.1 | 2.8 | 5.5 |
| Isolencine | 4.9 | 6.3 | 5.4 |
| Leucine | 6.6 | 9.4 | 9.6 |
| Lysine | 5.6 | 9.4 | 7.1 |
| Methionine | 1.2 | 3.5 | 3.7 |
| Phenylalanine | 4.3 | 4.3 | 4.4 |
| Threonine | 3.3 | 4.7 | 4.4 |
| Tryptophan | 1.2 | 1.1 | — |
| Valine | 4.7 | 6.5 | 6.7 |

TABLE 11

Trace Element Analysis of *T. denitrificans* Whole Cells Grown on $H_2S$

| | ppm (wt) |
|---|---|
| Fe | 7530 |
| Zn | 140 |
| Mg | 5800 |
| Cu | 90 |
| Ca | 3550 |
| Mn | 1710 |
| Na | 3330 |
| K | 1670 |
| Total Ash | 12% |
| Total Sulfur | 0.9% |

Mutant Strains

The present invention includes not only the use of wild strains of *T. denitrificans* such as ATCC 23646 (American Type Culture Collection, Rockville, Md.), but also mutant strains. For example, sulfide tolerant strains of *T. denitrificans* are desirable to make the proposed microbial gas desulfurization process more resistant to upset from excess $H_2S$ feed and possibly more tolerant of other sulfur compounds. A biocide resistant strain could provide a means of controlling heterotrophic contamination and therefore produce a microbially pure biomass product without the expense of maintaining aseptic conditions by sterilization of feed streams. Therefore, the term *T. denitrificans* as used herein and in the claims includes mutants thereof.

Continuous Flow Reactor with Biomass Recycle

A simple CSTR is an economically impractical reactor configuration with respect to volumetric productivity for the proposed microbial gas desulfurization process except where very small amounts of $H_2S$ are removed. However, a completely mixed, homogeneous environment for the cells is required to avoid localized inhibitory concentrations of sulfide. The most practical reactor configuration presently contemplated for a microbial gas desulfurization process based on *T. denitrificans* is a CSTR with biomass recycle. Recycle of the biomass allows much higher biomass concentrations to be maintained in the reactor. In addition, with biomass recycle, the hydraulic retention time and biomass retention time are decoupled. Therefore, high dilution rates can be used to replenish the culture medium and control the environment of the cells. Biomass concentration and the quality of the cells' environment will be the two most important variables in maximizing volumetric productivity while maintaining reactor stability. With cell recycle, these two variables are independently controlled.

For a CSTR with biomass recycle, the microbial cells must continuously be harvested from the reactor liquid waste stream. The more common methods of continuous harvesting of microbial cells include continuous centrifugation and tangential flow filtration. An alternative to harvesting and recycle of free cell biomass is the use of an immobilized biomass which is the preferred embodiment of the present invention as will be described hereinafter. If the immobilization matrix is sufficiently dense, biomass from the reactor effluent may be harvested by low gravity sedimentation. An immobilization matrix appropriate for growing cells must allow release of new cells into the surrounding medium. Therefore, the reactor effluent will contain both immobilized cells which could be readily recovered and recycled and free cells. If the free cells are to represent a process credit, they must be recovered. Therefore, even when immobilized cells are utilized, a free cell recovery problem still exists. However, since these cells are not recycled back to the reactor, treatment of the process stream (with a flocculating agent, for example) to improve sedimentation properties can be tolerated.

It was noted previously that a facultative organism offers advantages in versatility in a microbial gas desulfurization process. One of these advantages is revealed in the use of a porous immobilization matrix for the $T.$ $denitrificans$ biomass. Oxygen is only a sparingly soluble gas. At 30° C. and at saturation with air at 1 atmosphere, the concentration of oxygen in the culture medium characteristic of this process is on the order of 200–250 $\mu M$. Therefore, the driving force for mass transfer of $O_2$ into the immobilization matrix is relatively low. Therefore, in a purely aerobic system only the outermost fraction of the matrix volume may be populated with metabolically active cells. Research has shown that $T.$ $denitrificans$ will preferentially use oxygen as an oxidant in the presence of $NO_3^-$; however, $NO_3^-$ is immediately utilized when $O_2$ is depleted. The incorporation of nitrate in the culture medium at concentrations of only a few mM would result in a much higher driving force for mass transfer of $NO_3^-$ into the matrix than $O_2$. Therefore, in the presence of a small concentration of $NO_3^-$ the entire void volume of the immobilization matrix could be populated with metabolically active cells. The interior of the matrix would operate anaerobically while the exterior operates aerobically. This is hereafter referred to as a mixed aerobic/anaerobic system. The details of anaerobic metabolism of $H_2S$ in $T.$ $denitrificans$ have been described in a previous patent application (see U.S. Patent Application Ser. No. 787,219, filed Oct. 15, 1985).

The particular immobilization matrix does not form a part of the present invention and any known matrix material may be used which is suitable for the $T.$ $denitrificans$. By way of example only, see U.S. Pat. Nos. 4,153,510 and 4,286,061. Also, any suitable procedure well known in the prior art for immobilizing $T.$ $denitrificans$ cells on the matrix material can be used in the present invention as long as the cells may grow and divide while releasing new cells from the matrix.

Referring now to FIG. 1, the immobilized biomass is loaded into the reactor 10 which is filled with maintenance medium without thiosulfate. A limited amount of nitrate may be incorporated in the medium if a mixed aerobic/anaerobic metabolism is desired in the immobilization matrix. The hydrogen sulfide containing gas is passed into the reactor through line 12 and the treated gas with the $H_2S$ removed flows out line 14. Air is introduced into the reactor through line 11. The maintenance medium and immobilized biomass (the slurry) are stirred by the mixer 16 in order to achieve homogeneity, avoid localized inhibitory concentrations of sulfide and obtain good mass transfer.

Withdrawn from the reactor 10 is a slurry stream 18 which contains partially spent nutrient, free floating bacteria which have been expelled from the immobilizing support material and the dissolved sulfate formed in the reactor during the $H_2S$ removal process. A form of filtration may be employed to prevent the immobilized biomass from being withdrawn from the reactor along with the slurry. Alternatively, immobilized biomass withdrawn from the reactor along with the slurry is removed from the slurry in separator 20 and recycled to the reactor through line 22. This separator 20, for example, may be a conventional settling basin or hydrocyclone.

The slurry from the separator 20 is then passed to the settler 24 through line 26 to perform the removal of the free cell bacterial biomass. The preferred method of accomplishing this removal is by introducing a flocculating agent as indicated at 28 into the slurry to assist in the agglomeration and settling of the bacterial biomass. The bacterial biomass product is then removed from the settler as indicated at 30. The remaining liquid from the settler 24 now contains the spent nutrient and the sulfate. This liquid is passed through line 32 into the evaporator/fractional crystallizer 34. In the evaporator/fractional crystallizer, the process is controlled depending upon the relative concentrations of the sulfate and the remaining nutrients in the liquid such that only the sulfate is crystallized or such that the crystallized sulfate will contain only that amount of nutrient which has also been crystallized which can be tolerated in the sulfate product depending upon its intended end use. The product from the evaporator/ fractional crystallizer 34 is passed through line 36 to the separator 38 where the crystals are separated from the remaining liquid. The separated crystals containing primarily the sulfate is removed from the settler 38 through line 40. The liquid from the settler 38 contains primarily only the remaining nutrient materials which were present in the withdrawn spent nutrient. This liquid is recycled through line 42 to the reactor 10 along with fresh nutrient introduced through line 44 to replenish the spent nutrient. As shown in FIG. 1, the system for practicing this invention includes a temperature controlling heat exchanger 46 in which the medium being fed into the reactor 10 is controlled to a temperature of about 30° C. if wild type $T.$ $denitrificans$ is utilized or a higher temperature if a temperature tolerant strain is utilized. It may also be advantageous to precondition the makeup medium being introduced through line 44 to the optimal temperature. Further measures which can be employed to control temperature is to precondition the entering gas 12 to the optimal temperature, include a heat exchanger within the reactor 10 and insulate reactor 10.

For the purpose of giving a specific example of the present invention, the treatment of $25 \times 10^6$ standard cubic feed/day ($7.08 \times 10^8$ standard liters/day) of natural gas at 600 psig (42 atmospheres or 4238 kilopascals absolute) containing 1.5 mol % $H_2S$ will be used. The aerobic process of the present invention could not normally be used to directly remove the $H_2S$ since the oxygen would contaminate the natural gas. Therefore, a conventional amine plant would be used to treat the natural gas and remove the H₂S along with CO₂. The amine plant would remove $1.87 \times 10^4$ gram-moles of H₂S per hour. This H₂S plus any accompanying CO₂ removed represents the feed stream 12 to the reactor 10. If a stable loading (sulfide limiting conditions) of 10.0 millimols H₂S per hour per gram biomass is assumed, then $1.87 \times 10^6$ g of *T. denitrificans* biomass will be required to treat the gas stream. With a suitable choice of immobilization matrix, immobilized whole cell reactors 10 can be operated with 40% slurries of porous immobilization beads with low rates of attrition. Furthermore, the beads can develop internal populations of viable cells which pack the beads to 50% of their theoretical packing density. However, to be conservative, a 20% slurry of 200 micron beads with a maximum packing density of 25% of theoretical is assumed. This small bead diameter is selected to minimize internal mass transfer resistances. If a *T. denitrificans* cell is idealized as a cylinder with a diameter of 0.5 micron and length of 1.5 microns, a 200 micron bead would contain $1.67 \times 10^7$ cells at maximum packing. A 20% slurry of beads would therefore contain $1.33 \times 10^{14}$ cells per liter. A viable cell density of $10^9$ cells per milliliter is roughly equivalent to 0.5 grams dry weight of biomass per liter. Therefore, a 20% slurry of 200 micron beads with maximum cell packing would contain 67 grams per liter of immobilized cells. To be conservative, 50 grams per liter is chosen as a design basis. Therefore, if the free cell biomass is neglected, a total bubble free culture volume of $3.7 \times 10^4$ liters will be required to treat the gas stream described above.

The economics of a microbial gas desulfurization process are obviously strongly influenced by the volumetric productivity of the bioreactor. A second important factor is the dilution rate at which the reactor is operated. Process economics are favored by lower dilution rates. The reactor effluent must be processed to recover biomass and the sulfate salt, both of which may be taken as a process credit. Lower dilution rates result in a lower rate of flow of the effluent stream and increased concentrations of free cell biomass and sulfate which reduce processing costs. In addition, lower dilution rates decrease pumping costs. However, the reduction of dilution rate to improve process economics has a limitation dictated by the tolerance of the biomass for the accumulating sulfate salt in the culture medium. The maximum concentration of the sulfate salt which can be tolerated without significant inhibition of growth, and therefore H₂S oxidation, will determine the minimum dilution rate at which the reactor can be operated. As noted above, some control can be exerted by choice of the sulfate counter ion which is determined primarily by the hydroxide counter ion in the pH adjusting solution.

I claim:

1. A method for treating a gas stream containing hydrogen sulfide to remove said hydrogen sulfide comprising the steps of:
   a. culturing *T. denitrificans* in the absence of H₂S in a maintenance medium containing a quantity of thiosulfate to produce a desired population of *T.denitrificans*, thereby reducing said quantity of thiosulfate and forming a slurry of *T. denitrificans* in maintenance medium,
   b. removing any thiosulfate which may remain in said slurry,
   c. flowing said gas stream and oxygen through said slurry in a reactor whereby said *T. denitridicans* removes said hydrogen sulfide under aerobic conditions and produces sulfate and whereby said population of *T. denitrificans* increases to produce excess *T. denitrificans*, the ratio of gas stream flow to the quantity of *T. denitrificans* being such that the average maximum loading of H₂S is no greater than 20 millimoles of H₂S per hour per gram dry weight of *T. denitrificans* and the quantity of O₂ is maintained at a level of at least 25 μM,
   d. removing a portion of said slurry from said reactor, said slurry containing excess *T. denitrificans* and sulfate,
   e. removing at least a portion of said excess *T. denitrificans* and at least a portion of said sulfate from said removed slurry thereby leaving a remaining slurry, and
   f. recycling said remaining slurry back to said reactor.

2. A method for treating a gas stream containing hydrogen sulfide to remove said hydrogen sulfide comprising the steps of:
   a. culturing *T. denitrificans* in the absence of H₂S in a maintenance medium containing a quantity of thiosulfate to produce a desired population of *T. denitrificans*, and to reduce said quantity of thiosulfate,
   b. removing any thiosulfate which may remain,
   c. immobilizing said population of *T. denitrificans* in immobilization matrices,
   d. introducing said population of *T. denitrificans* in said immobilization matrices into a reactor containing maintenance medium free of thiosulfate thus creating a slurry,
   e. flowing said gas stream and oxygen through said slurry in said reactor whereby said *T. denitrificans* removes said hydrogen sulfide under aerobic conditions and produces sulfate and whereby said population of *T. denitrificans* increases to produce excess *T. denitrificans* which are released from said immobilization matrices, the ratio of gas stream flow to the quantity of *T. denitrificans* being such that the average maximum loading of H₂S is no greater than 20 millimoles of H₂S per hour per gram dry weight of *T. denitrificans* and the quantity of O₂ is maintained at a level of at least 25 μM,
   f. removing a portion of said slurry from said reactor, said removed slurry containing a portion of said immobilization matrices containing *T. denitrificans* and a portion of said excess *T. denitrificans* which have been released from said immobilization matrices and a portion of said produced sulfate and a portion of said maintenance medium,
   g. removing from said slurry and recycling to said reactor said immobilization matrices containing said *T. denitrificans* and producing a remaining slurry,
   h. removing said remaining slurry said excess *T. denitrificans* to produce a *T. denitrificans* biomass product and a spent maintenance medium solution containing sulfate, and
   i. removing at least a portion of said sulfate from said spent maintenance medium solution and recycling said spent maintenance medium solution back to said reactor.

3. A method as recited in claim 2 and further including the step of introducing fresh maintenance medium to said reactor.

4. A method as recited in claim 2 wherein the temperature in said reactor is controlled to about 30° C.

5. A method as recited in claim 4 and further including the step of introducing fresh maintenance medium to said reactor.

6. A method as recited in claim 2 wherein said maintenance medium includes nitrate whereby said *T. denitrificans* on the outermost portion of said immobilization matrices will function aerobically and the *T. denitrificans* on the innermost portions of said matrices will function anaerobically through the metabolism of nitrate.

7. A method as recited in claim 3 wherein said maintenance medium includes nitrate whereby said *T. denitrificans* on the outermost portion of said immobilization matrices will function aerobically and the *T. denitrificans* on the innermost portions of said matrices will function anaerobically through the metabolism of nitrate.

8. A method as recited in claim 4 wherein said maintenance medium includes nitrate whereby said *T. denitrificans* on the outermost portion of said immobilization matrices will function aerobically and the *T. denitrificans* on the innermost portions of said matrices will function anaerobically through the metabolism of nitrate.

9. A method as recited in claim 5 wherein said maintenance medium includes nitrate whereby said *T. denitrificans* on the outermost portion of said immobilization matrices will function aerobically and the *T. denitrificans* on the innermost portions of said matrices will function anaerobically through the metabolism of nitrate.

10. A method as recited in claim 3 wherein said maintenance medium further contains nitrate as a terminal electron acceptor, bicarbonate as a carbon source and ammonium as the nitrogen source.

11. A method as recited in claim 2 wherein hydroxide is added to said slurry for pH control between 6.2 and 7.0.

12. A method as recited in claim 2 wherein said gas stream and oxygen flow through said slurry in step (e) further contains up to 5% $CO_2$ to supplement the carbon supply.

* * * * *